US005705639A

United States Patent [19]

Shapiro

[11] Patent Number: 5,705,639
[45] Date of Patent: Jan. 6, 1998

[54] PROCESS TO PREPARE HERBICIDAL BICYCLIC TRIAZOLES

[75] Inventor: Rafael Shapiro, Wilmington, Del.

[73] Assignee: E. I. du Pont de Nemours and Company, Wilmington, Del.

[21] Appl. No.: 525,502

[22] PCT Filed: Mar. 8, 1994

[86] PCT No.: PCT/US94/02497

§ 371 Date: Sep. 21, 1995

§ 102(e) Date: Sep. 21, 1995

[87] PCT Pub. No.: WO94/22828

PCT Pub. Date: Oct. 13, 1994

Related U.S. Application Data

[63] Continuation-in-part of Ser. No. 37,217, Mar. 26, 1993, abandoned.

[51] Int. Cl.[6] .................. C07D 211/72; C07D 265/30; C07D 471/04; C07D 498/04
[52] U.S. Cl. .................. 544/47; 544/73; 544/105; 544/135; 544/137; 544/153; 544/164; 546/119; 546/196; 546/198; 546/223; 546/244
[58] Field of Search .................. 544/47, 73, 105, 544/135, 137, 153, 164; 546/119, 196, 198, 223, 244

[56] References Cited

U.S. PATENT DOCUMENTS

| | | | |
|---|---|---|---|
| 4,080,192 | 3/1978 | Wolf | 71/93 |
| 4,139,364 | 2/1979 | Wolf | 71/92 |
| 4,213,773 | 7/1980 | Wolf | 71/92 |
| 4,881,967 | 11/1989 | Semple | 71/92 |
| 4,925,481 | 5/1990 | Blume et al. | 71/92 |

FOREIGN PATENT DOCUMENTS 0 317 947  5/1989  European Pat. Off.  ...... C07D 471/04

OTHER PUBLICATIONS

Barluenga, J. et al, *Synthesis*, 831–832 (1984).
Radlick, P. et al, *Synthesis*, 290–291 (1974).
Kwok, R. et al., *J. Org. Chem.*, 32, 738–740 (1967).
Moriconi, E.J. et al., *J. Org. Chem.*, 33(5), 2109–2111 (1968).

*Primary Examiner*—Philip I. Datlow

[57] ABSTRACT

This invention includes compounds of Formula II and IV and a process for preparing Formula I compounds by first preparing the compounds of Formula IV and then further reacting to form the compounds of Formula II and further reacting to prepare the compounds of Formula I wherein Q, Z, $R^2$ are as defined within.

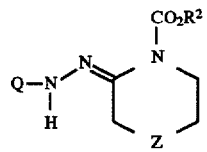

II

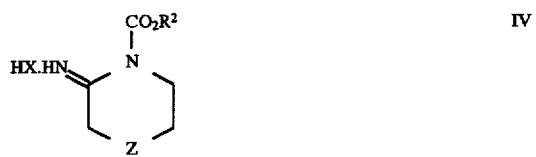

IV

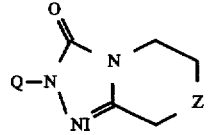

11 Claims, No Drawings

PROCESS TO PREPARE HERBICIDAL BICYCLIC TRIAZOLES

This application was filed in the PCT as PCT/US94/02497 on Mar. 8, 1994 designating among other countries the USA and is a continuation in part of U.S. Ser. No. 08/037,217 filed Mar. 26, 1993, now abandoned.

BACKGROUND OF THE INVENTION

U.S. Pat. No. 4,925,481, U.S. Pat. No. 4,213,773 and U.S. Pat. No. 4,881,967 disclose herbicidal tetrahydrotriazolopyridin-3-ones and methods for preparation, but do not disclose the instant process.

SUMMARY OF THE INVENTION

The invention pertains to a process to prepare compounds of Formula I wherein Q is

Q-1, Q-2, Q-3, Q-4

$R^1$ is H, halogen, OH, $C_1$–$C_6$ alkyl, $C_1$–Chaloalcyl, $C_1$–Calkoxy, $C_1$–$C_6$ haloalkoxy, $C_1$–$C_6$ alkylthio, $C_1$–$C_6$ haloalkylthio, $C_2$–$C_6$ alkenyloxy, $C_2$–$C_6$ alkenylthio, $C_2$–$C_6$ haloalkenyloxy, $C_2$–$C_6$ haloalkenylthio, $C_3$–$C_6$ alkynyloxy, $C_3$–$C_6$ alkynylthio, $C_3$–$C_6$ haloalkynyloxy, $C_3$–$C_6$ haloalkynylthio, $C_2$–$C_6$ alkylcarbonyl, $C_2$–$C_6$ alkoxycarbonyl, $C_4$–$C_8$alkenyloxycarbonyl, $C_3$–$C_8$ alkylcarbonylalkoxy, $C_3$–$C_8$ alkylcarbonylalkylthio, $C_3$–$C_8$ alkoxycarbonylalkoxy, $C_3$–$C_8$ alkoxycarbonylalkylthio, $C_5$–$C_8$ alkenyloxycarbonylalkoxy, $C_5$–$C_8$ alkenyloxycarbonylalkylthio, phenoxy and phenylthio where the phenyl groups are optionally substituted with halogen;

$R^3$ is H, $C_1$–$C_6$ alkyl, $C_1$–$C_6$ haloalkyl, $C_2$–$C_6$ alkoxyalkyl, $C_3$–$C_6$ alkenyl, $C_3$–$C_6$ alkynyl and $CH_2CH \overset{O}{-\!\!\!-\!\!\!-} CH_2$;

$R^4$ is H, $C_1$–$C_3$ alkyl and halogen;

$R^5$ is H, halogen, $C_1$–$C_3$ alkyl, $C_1$–$C_3$ haloalkyl, cyclopropyl, vinyl, $C_2$ alkynyl, CN, C(O)$R^6$, C(O)$_2R^6$, C(O)NR$^6$R$^7$, CR$^8$R$^9$CN, CR$^8$R$^9$C(O)R$^6$, CR$^8$R$^9$C(O)$_2R^6$, CR$^8$R$^9$C(O)NR$^6$R$^7$, CHR$^8$OH, CHR$^8$OC(O)R$^6$ and OCHR$^8$OC(O)NR$^6$R$^7$;

$R^6$ and $R^7$ are independently H and $C_1$–$C_4$ alkyl;

$R^8$ and $R^9$ are independently H and $C_1$–$C_4$ alkyl;

W is O and S;

Z is CH$_2$ and);

m is 1–5; and n is 1–3; when m or n are greater than 1, $R^1$ may be the same or independently selected from the defined substituents;

which involves the following reactions:

first, reacting compounds of Formula V $$NC\frown Z \frown NHCO_2R^2 \quad V$$

wherein $R^2$ is $C_1$–$C_6$ alkyl; with an anhydrous acid to produce compounds of Formula IV $$\text{HX.HN} \overset{CO_2R^2}{\underset{Z}{\diagup N \diagdown}} \quad IV$$

wherein X is Cl or Br and $R^2$ is described above; second, reacting compounds of Formula IV with Formula III hydrazines or salts thereof $$Q-NHNH_2 \quad (III)$$

wherein Q is defined above;

to produce compounds of Formula II

II wherein $R^2$ is defined above; and third, heating compounds of Formula II in liquid form optionally in the presence of an acid to produce Formula I compounds at 0°–150° C. with or without a solvent

I wherein Q and Z are defined above.

This invention further pertains to novel Formulae II and IV intermediates

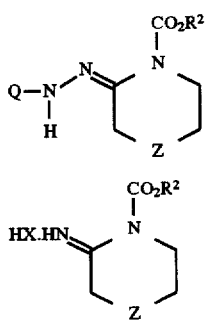

wherein Q, R², and X are defined above.

In the above definitions, the term "alkyl", used either alone or in compound words such as "alkylthio" or "haloalkyl", includes straight chain or branched alkyl, such as methyl, ethyl, n-propyl, isopropyl and the different butyl, pentyl, and hexyl isomers. "Alkoxy" used either alone or in compound words such as "haloalkoxy" includes methoxy, ethoxy, n-propoxy, isopropoxy, and the different butoxy, pentoxy, and hexyloxy isomers. "Alkenyl" used either alone or in compound words such as "haloalkenyl" or "alkenylthio" includes straight chain or branched alkenes, such as vinyl, 1-propenyl, 2-propenyl, 3-propenyl and the different butenyl, pentenyl, and hexenyl isomers. "Alkynyl" used either alone or in compound words such as "haloalkynyl" or "alkynylthio" includes straight or branched alkynes, such as 1-propynyl, 3-propynyl, and the different butynyl, pentynyl, and hexynyl isomers. "Alkylthio" includes methylthio, ethylthio, and the different propylthio, butylthio, pentylthio, and hexylthio isomers.

The term "halogen", used either alone or in compound words such as "haloalkyl", means fluorine, chlorine, bromine or iodine. Further, when used in compound words such as "haloalkyl" said alkyl can be partially or fully substituted with halogen atoms, which can be the same or different. Examples of haloalkyl include $CF_3$, $CH_2CH_2F$, $CF_2CF_3$, $CH_2CHFCl$, and $CHBrCH_3$. The terms "haloalkenyl" and "haloalkynyl" are defined analogously to the term "haloalkyl".

The total number of carbon atoms in a substituent group is indicated by the "$C_i$–$C_j$" prefix where i and j are numbers from 1 to 8. For example, $C_3$ alkynyloxy designates $OCH_2C\equiv CH$, and $C_4$ alkynyloxy includes $OCH_2C\equiv CCH_3$, $OCH_2CH_2C\equiv CH$ and $OCH(CH_3)C\equiv CH$; $C_2$ alkylcarbonyl designates $C(O)CH_3$, and $C_4$ alkylcarbonyl includes $C(O)CH_2CH_2CH_3$ and $C(O)CH(CH_3)_2$; $C_2$ alkoxycarbonyl designates $C(O)_2CH_3$, and $C_4$ alkoxycarbonyl includes $C(O)_2CH_2CH_2CH_3$ and $C(O)_2CH(CH_3)_2$; $C_3$ alkylcarbonylalkoxy designates $OCH_2C(O)CH_3$, and $C_4$ alkylcarbonylalkoxy includes $OCH_2C(O)CH_2CH_3$, $OCH(CH_3)C(O)CH_3$, and $OCH_2CH_2C(O)CH_3$; $C_3$ alkoxycarbonylalkoxy designates $OCH_2C(O)_2CH_3$, and $C_4$ alkoxycarbonylalkoxy includes $OCH_2C(O)_2CH_2CH_3$, $OCH(CH_3)C(O)_2CH_3$, and $OCH_2CH_2C(O)_2CH_3$; $C_3$ alkylcarbonylalkylthio designates $SCH_2C(O)CH_3$, and $C_4$ alkylcarbonylalkylthio includes $SCH_2C(O)CH_2CH_3$, $SCH(CH_3)C(O)CH_3$, and $SCH_2CH_2C(O)CH_3$; and as a final example $C_3$ alkylcarbonylalkylthio designates $SCH_2C(O)_2CH_3$, and $C_4$ alkylcarbonylalkylthio includes $SCH_2C(O)_2CH_2CH_3$, $SCH(CH_3)C(O)_2CH_3$, and $SCH_2CH_2C(O)_2CH_3$.

When a compound is substituted with a substituent bearing a subscript that indicates the number of said substituents can exceed 1, said substituents (when they exceed 1) are independently selected from the group of defined substituents.

Specifically preferred processes for the greatest utility of their products are:

A) The process to prepare Formula I compounds wherein Q is Q-1.

B) The process of Preferred A to prepare Formula I compounds selected from the group:
2-[2,4-dichloro-5-(2-propynyloxy)phenyl]-5,6,7,8-tetrahydro-1,2,4-triazolo[4,3-a]pyridin-3(2H)-one;
ethyl[[2-chloro-4-fluoro-5-(5,6,7,8-tetrahydro-3-oxo-1,2,4-triazolo[4,3-a]pyridin-2(3H)-yl)phenyl]thio] acetate; and
2-(2,4-dichloro-5-hydroxyphenyl)-5,6,7,8-tetrahydro-1,2,4-triazolo[4,3a]pyridin-3(2H)-one.

C) The process to prepare Formula I compounds wherein Q is Q-2.

D) The process of Preferred C to prepare the Formula I compound:
2-(5,7-dichloro-2,3-dihydro-2-methyl-4-benzofuranyl)-5,6,7,8-tetrahydro-1,2,4-triazolo[4,3-a]-pyridin-3(2H)-one.

E) The process to prepare Formula I compounds wherein Q is Q-3.

F) The process to prepare Formula I compounds wherein Q is Q-4.

G) The process of Preferred F to prepare the Formula I compound:
6-(5,6,7,8-tetrahydro-3-oxo-1,2,4-triazolo[4,3-a] pyridin-2(3H)-yl)4-(2-propynyl)-2H-1,4-benzoxazin-3(4H)-one.

Compounds produced by the process of the invention are active herbicides for selective and/or general broadleaf and grass weeds control in all plantation crops which include coffee, cocoa, oil palm, rubber, sugar cane, citrus, grapes, fruit trees, nut trees, banana, plantain, pineapple, conifers, e.g., loblolly pine, and turf species Kentucky bluegrass, St. Augustine grass, Kentucky fescue and bermudagrass.

The intermediates of the present invention are useful as such in the process of the invention to produce the active herbicides.

DETAILED DESCRIPTION OF THE INVENTION

The first stage (a) of the process (Scheme I) is as a rule carried out by contacting one or more equivalents of an anhydrous hydrogen halide, preferably 2 to 2.5 equivalents of hydrogen chloride, at a temperature between –40° C. and 40° C., preferably at 5°–15° C., with a compound of Formula V, preferably the methyl carbamate, either in an inert hydrocarbon, chlorinated hydrocarbon, or ethereal solvent, preferably toluene, with or without solvent. The solvent is advantageously used in an mount from 100 to 2000 percent by weight, based on starting material V, and the reaction may be conducted at atmospheric or superatmospheric pressure in either a continuous or a batchwise mode. The products of Formula IV are generally isolated by removal of excess hydrogen halide under reduced pressure followed by removal of solvent or filtration and washing with a suitable oxygenated solvent such as tetrahydrofuran. Alternatively, they may be used without purification following the purge of excess hydrogen halide. Carbamates of Formula V are either known or can be prepared by various methods known to one skilled in the art. For example, Synthesis, (1984) 831 describes the preparation of Formula V carbamates by amidomercuration-reductive alkylation of alkenes and amides.

Scheme I

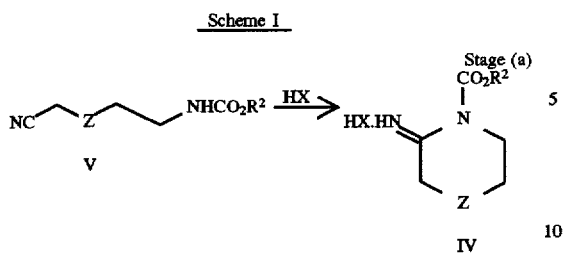

wherein R², X, and Z are as described previously.

The second stage (b) of the process, illustrated in Scheme II, is as a rule carried out by contacting the hydrohalide salt of Formula IV with an approximately equivalent molar amount of a hydrazine compound of Formula III or a salt thereof and a sufficient amount of acid binding agent to maintain an effective pH of 3.5 to 7.0, preferably at 4.5 to 5.5, in a suitable non-reactive solvent, preferably, but not limited to, acetonitrile or alcohols such as methanol, at a temperature between −40° and 80° C., preferably at −20° C. to 30° C. The acid-binding agent used may be any weakly-basic anhydrous material but is preferably a weak tertiary amine base such as pyridine or an alkali metal carboxylic acid salt such as sodium acetate, and is preferably used in amounts of between 0.5 to 1.5 equivalents, based on the total amount of acid bound in the compounds of Formulae III and IV. Hydrazines of Formula III are either known or can be prepared by various methods known to one skilled in the art. For example, U.S. Pat. No. 4,881,967 and references cited therein, describe the preparation of hydrazines by diazotization of appropriately substituted amines known in the art.

Scheme II

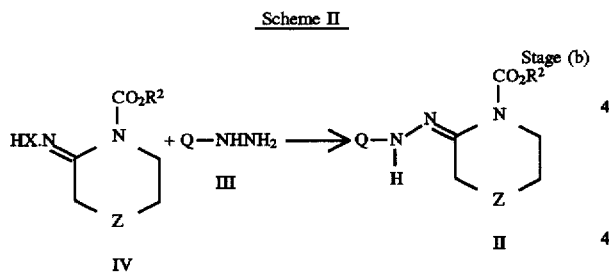

wherein Q is as described previously.

Preparation of Formula I compounds (Stage (c)) is as a rule carried out by allowing a compound of Formula II to react, optionally with a solvent, at a temperature between 0° and 150° C., advantageously in the presence of an acidic catalyst, either at atmospheric, subatmospheric, or superatmospheric pressures (Scheme III). A wide range of solvents may be used, but are preferably non-ketonic, neutral or only weakly acidic. Especially preferred are toluene, acetone, ethyl acetate, and isopropyl acetate, preferably used in amounts of between 100 and 2000 percent. The reaction is optionally acid-catalyzed, and 0.01 to 100 molar equivalents of formic, acetic, propionic acid and the like may be used, preferably using 0.1 to 3 equivalents, preferably operating the process at temperatures from 25°–100° C. The end product of the process, a compound of Formula I, is then isolated by cooling the reaction mixture, optionally adding a non-polar solvent, such as hexanes, and filtering the precipitated product.

Scheme III

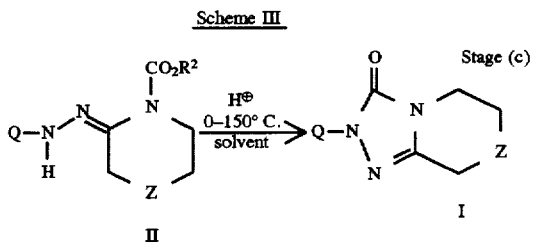

Alternatively, Formula I compounds may be prepared by heating the reaction mixture of Stage (b) from 25°–150° C., but is preferably carried out by first isolating the intermediate compounds of Formula II and conducting the reaction as described for Stage (c).

EXAMPLE 1

Step A

Preparation of methyl 2-imino-1-piperidinecarboxylate hydrochloride

Bromine (6.5 kg) is added subsurface to a solution of 5.1 kg of 5-cyano-valeramide and 4.45 kg of sodium methylate in 27.5 kg of methanol at 0°–5 ° C. The resulting mixture is transferred slowly to 24 kg of hot (60° C.) methanol to maintain the temperature at 50°–65 ° C. The majority of the methanol is removed by distillation, toluene (30 kg) is added, and the distillation is continued until all of the methanol is removed. The mixture is then filtered to obtain an approximately 18% (wt/wt) solution of methyl 4-cyanobutyl carbamate in toluene. A portion of this solution (259 g) is maintained at 15°–20° C. while 33 g of anhydrous hydrogen chloride is bubbled in during two hours. The two-phase mixture is then purged of excess HCl at 150 torr and 100 mL of tetrahydrofuran is added. The product is filtered and washed with tetrahydrofuran to remove residual HCl. The title compound is thus obtained as 53 g (95%) of a white crystalline solid, m.p. 118°–119 ° C. (dec). $^1$H NMR (CDCl$_3$)δ1.7 (t, 2H), 1.8 (t, 2H), 3.15 (t, 2H), 3.8 (t,2H), 3.82 (s, 3H), 10.2 (br s, 1H), 12.75 (br s, 1H).

Step B

Preparation of methyl 2-[[2,4-dichloro-5-(2-propynyloxy)phenyl]-hydrazono]-1-piperidinecarboxylate To a mixture of 12.3 g of anhydrous sodium acetate and 80 mL of acetonitrile is added 13.3 g of 91% 2,4-dichloro-5-(propargyloxy)phenyl-hydrazine hydrochloride and, after 30 minutes of vigorous stirring, the mixture is cooled to 0°–5° C. before adding 10.0 g of the product from Step A. The mixture is stirred vigorously for 1 h at 5°–10 ° C. and is then poured into 200 mL of cold water. The product is filtered, washed with 30 mL of cold water and then with 30 mL of cold isopropanol, and dried to provide 16.0 g (95%) of the title compound as a solid, m.p. 137°–138° C. $^1$H NMR (CDCl$_3$) δ5 1.74 (m, 2H), 1.82 (m, 2H), 2.46 (t, 2H, J=6Hz), 2.52 (d, 1H, J=2.4Hz), 3.68 (t, 2H, J=6Hz), 3.73 (s, 3H), 4.75 (d, 2H, J=2.4Hz), 7.13 (s, 1H), 7.23 (s, 1H), 7.26 (br s, 1H).

Step C

Preparation of 2-[2,4-dichloro-5-(2-propynyloxy) phenyl]-5,6,7,8-tetrahydro-1,2,4-triazolo[4,3-a]-pyridin-3(2H)-one A mixture of 10.0 g of the product from Step B and 0.50 g of glacial acetic acid in 50 mL of toluene is heated at 100°

C. for 2 h while removing methanol vapor with a stream of nitrogen. Hexane (50 mL) is added at 70° C. and the product is filtered at 25° C. and washed with hexanes to provide 8.0 g (94%) of the title compound, m.p. 168°–169° C. $^1$H NMR (CDCl$_3$) δ1.9 (m, 4H), 2.55 (t, 1H, J=2.4Hz), 2.74 (t, 2H, J=6Hz), 3.67 (t, 2H, J=6Hz), 4.74 (d, 2H, J=2.4Hz), 7.13 (s, 1H), 7.50 (s, 1H).

EXAMPLE 2

Step A

Preparation of methyl 2-[2,4-dichloro-5-hydroxyphenyl)hydrazonol-1piperidinecarboxylate A mixture of 18.5 g of sodium acetate and 320 mL of dry methanol is cooled to –20° C. and 28.8 g of the product from Example 1, Step A is added, followed by 34.8 g of 96% pure 2,4-dichloro-5-hydrazinophenol hydrochloride. The mixture is stirred for 1 h at –10° to 0° C. and then is poured into 500 mL of ice water. The product is filtered, washed with three 100 mL portions of water and dried in vacuo to provide 44.6 g of the title compound as an orange solid, m.p. 158°–159° C. $^1$H NMR (DMSO-d$_6$) δ1.7 (m, 4H), 2.5 (t, 2H, J=5.4Hz), 3.57 (t, 2H, J=5.4Hz), 3.64 (s, 3H), 7.00 (s, 1H), 7.25 (s, 1H), 8.15 (br s, 1H), 10.3 (br s, 1H).

Step B

Preparation of 2-(2,4-dichloro-5-hydroxyphenyl)-5,6,7,8-tetrahydro-1,2,4-triazolo[4,3-a]pyridin-3(2H)-one A mixture of 50 g of the product from Step A and 100 mL of a 5% solution of acetic acid in toluene is heated at 65°–70° C. for 3 h with removal of methanol by a stream of nitrogen. Hexanes (50 mL) is then added and the mixture is filtered at ambient temperature, washed sequentially with 50 mL of hexanes and two 50-mL portions of cold isopropanol, and dried to provide 37 g of the title compound, m.p. 214°–216° C. (218°–219° C. recrystallized from aq. EtOH). $^1$H NMR (DMSO-d$_6$) δ1.8 (m, 4H), 2.6 (t, 2H, J=6Hz), 3.50 (t, 2H, J=6Hz), 7.09 (s, 1H), 10.9 (br s, 1H).

What is claimed is:

1. A process for preparing compounds of the Formula IV

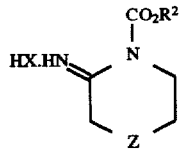

wherein X is Cl or Br, R$^2$ is C$_1$–C$_6$ alkyl, and Z is CH$_2$ or O comprising reacting a compound of Formula V

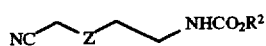

wherein R$^2$ and Z are as described above, with anhydrous HCl or HBr at –40° to 40° C.

2. The process of claim 1 further comprising reacting compounds of Formula IV with hydrazines of the Formula III or salts thereof

 (III)

in the presence of a suitable solvent and an acid binding agent at –40° to 80° C to produce compounds of Formula II

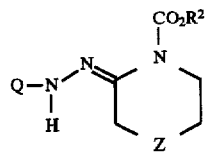

wherein Q is

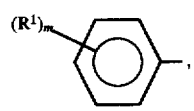 Q-1

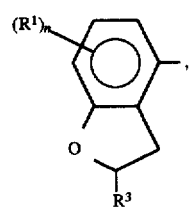 Q-2

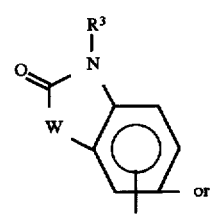 Q-3

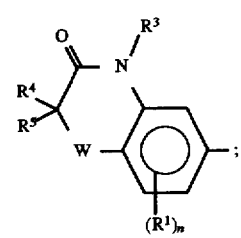 Q-4

R$^1$ is H, halogen, OH, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ haloalkylthio, C$_2$–C$_6$ alkenyloxy, C$_2$–C$_6$ alkenylthio, C$_2$–C$_6$ haloalkenyloxy, C$_2$–C$_6$ haloalkenylthio, C$_3$–C$_6$ alkynyloxy, C$_3$–C$_6$ alkynylthio, C$_3$–C$_6$ haloalkynyloxy, C$_3$–C$_6$ haloalkynylthio, C$_2$–C$_6$ alkylcarbonyl, C$_2$–C$_6$ alkoxycarbonyl, C$_4$–C$_8$ alkenyloxycarbonyl, C$_3$–C$_8$ alkylcarbonylalkoxy, C$_3$–C$_8$ alkylcarbonylalkylthio, C$_3$–C$_8$ alkoxycarbonylalkoxy, C$_3$–C$_8$ alkoxycarbonylalkylthio, C$_5$–C$_8$ alkenyloxycarbonylalkoxy, C$_5$–C$_8$ alkenyloxycarbonylalkylthio, phenoxy and phenylthio where the phenyl groups are optionally substituted with halogen;

R$^3$ is H, C$_1$–C$_6$ alkyl, C$_1$–C$_6$ haloalkyl, C$_2$–C$_6$ alkoxyalkyl, C$_3$–C$_6$ alkenyl, C$_3$–C$_6$ alkynyl and

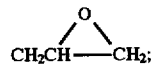

R$^4$ is H, C$_1$–C$_3$ alkyl and halogen;

R$^5$ is H, halogen, C$_1$–C$_3$ alkyl, C$_1$–C$_3$ haloalkyl, cyclopropyl, vinyl, C$_2$ alkynyl, CN, C(O)R$^6$, C(O)$_2$R$^6$, C(O)NR$^6$R$^7$, CR$^8$R$^9$CN, CR$^8$R$^9$C(O)R$^6$, CR$^8$R$^9$C(O)$_2$R$^6$, CR$^8$R$^9$C(O)NR$^6$R$^7$, CHR$^8$OH, CHR$^8$OC(O)R$^6$ and OCHR$^8$OC(O)NR$^6$R$^7$;

$R^6$ and $R^7$ are independently H or $C_1$–$C_4$ alkyl;

$R^8$ and $R^9$ are independently H or $C_1$–$C_4$ alkyl;

W is O or S;

Z is $CH_2$ or O;

m is 1–5; and n is 1–3; when m or n are greater than 1, $R^1$ may be the same or independently selected from the defined substituents.

3. The process of claim 2 further comprising reacting compounds of Formula II at 0° to 150° C. optionally in the presence of a solvent and an acid catalyst to produce compounds of Formula I

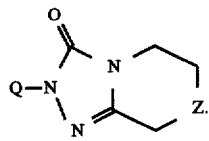

I

4. The process of claim 3 wherein Q is Q-1.

5. The process of claim 4 wherein the Formula I compound is selected from the group:

2-[2,4-dichloro-5-(2-propynyloxy)phenyl]-5,6,7,8-tetrahydro-1,2,4-triazolo[4,3-a]pyridin-3 (2H)-one;

ethyl [[2-chloro-4-fluoro-5-(5,6,7,8-tetrahydro-3-oxo-1,2,4-triazolo[4,3-a]pyridin-2(3H)-yl)phenyl]thio] acetate; and 2-(2,4-dichloro-5 -hydroxyphenyl)-5,6,7,8-tetrahydro-1,2,4-triazolo[4,3-a]pyridin-3(2H)-one.

6. The process of claim 3 wherein Q is Q-2.

7. The process of claim 3 wherein the Formula I compound is 2-(5,7-dichloro-2,3-dihydro-2-methyl-4-benzofuranyl)-5,6,7,8-tetrahydro-1,2,4-triazolo[4,3-a]-pyridin-3(2H)-one.

8. The process of claim 3 wherein Q is Q-3.

9. The process of claim 3 wherein Q is Q-4.

10. The process of claim 9 wherein the Formula I compound is 6-(5,6,7,8-tetrahydro-3-oxo-1,2,4-triazolo[4,3-a]pyridin-2(3H)-yl)-4-(2-propynyl)-2H -1,4-benzoxazin-3(4H)-one.

11. Compounds of the Formula II or IV

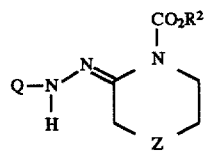

II

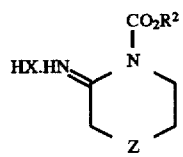

IV wherein Q is

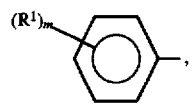

Q-1

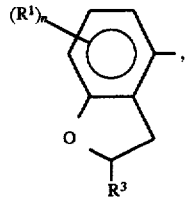

Q-2

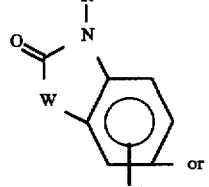

Q-3 or

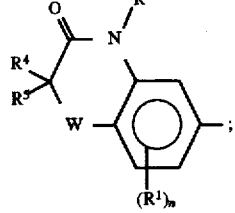

Q-4

$R^1$ is H, halogen, OH, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, $C_2$–$C_6$ alkenyloxy, $C_2$–$C_6$ alkenylthio, $C_2$–$C_6$ haloalkenyloxy, $C_2$–$C_6$ haloalkenylthio, $C_3$–$C_6$ alkynyloxy, $C_3$–$C_6$ alkynylthio, $C_3$–$C_6$ haloalkynyloxy, $C_3$–$C_6$ haloalkynylthio, $C_2$–$C_6$ alkylcarbonyl, $C_2$–$C_6$ alkoxycarbonyl, $C_4$–$C_8$ alkenyloxycarbonyl, $C_3$–$C_8$ alkylcarbonylalkoxy, $C_3$–$C_8$ alkylcarbonylalkylthio, $C_3$–$C_8$ alkoxycarbonylalkoxy, $C_3$–$C_8$ alkoxycarbonylalkylthio, $C_5$–$C_8$ alkenyloxycarbonylalkoxy, $C_5$–$C_8$ alkenyloxycarbonylalkylthio, phenoxy and phenylthio where the phenyl groups are optionally substituted with halogen;

$R^3$ is H, $C_1$–$C_6$ alkyl, $C_1$–$C_6$ haloalkyl, $C_2$–$C_6$ alkoxyalkyl, $C_3$–$C_6$ alkenyl, $C_3$–$C_6$ alkynyl and

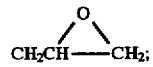

$R^4$ is H, $C_1$–$C_3$ alkyl and halogen;

$R^5$ is H, halogen, $C_1$–$C_3$ alkyl, $C_1$–$C_3$ haloalkyl, cyclopropyl, vinyl, $C_2$ alkynyl, CN, $C(O)R^6$, $C(O)_2R^6$, $C(O)NR^6R^7$, $CR^8R^9CN$, $CR^8R^9C(O)R^6$, $CR^8R^9C(O)_2R^6$, $CR^8R^9C(O)NR^6R^7$, $CHR^8OH$, $CHR^8OC(O)R^6$ and $OCHR^8OC(O)NR^6R^7$;

$R^6$ and $R^7$ are independently H and $C_1$–$C_4$ alkyl;

$R^8$ and $R^9$ are independently H and $C_1$–$C_4$ alkyl;

W is O and S;

X is Cl or Br;

Z is $CH_2$ or O;

m is 1–5; and n is 1–3; when m or n are greater than 1, $R^1$ may be the same or independently selected from the defined substituents.

* * * * *